United States Patent
Klimas

(10) Patent No.: US 11,883,466 B2
(45) Date of Patent: *Jan. 30, 2024

(54) METHOD OF TREATING PARKINSON'S DISEASE WITH INTRANASAL DELIVERY OF INSULIN AND GLUTATHIONE

(71) Applicant: Gateway Institute for Brain Research, LLC, Fort Lauderdale, FL (US)

(72) Inventor: Nancy Klimas, Miami, FL (US)

(73) Assignee: Gateway Institute for Brain Research, LLC, Fort Lauderdale, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/847,275

(22) Filed: Jun. 23, 2022

(65) Prior Publication Data

US 2022/0313788 A1    Oct. 6, 2022

Related U.S. Application Data

(62) Division of application No. 17/584,468, filed on Jan. 26, 2022.

(60) Provisional application No. 63/153,422, filed on Feb. 25, 2021.

(51) Int. Cl.
  *A61K 38/28*    (2006.01)
  *A61P 25/16*    (2006.01)
  *A61K 9/00*     (2006.01)
  *A61K 38/06*    (2006.01)

(52) U.S. Cl.
  CPC ............ *A61K 38/28* (2013.01); *A61K 9/0043* (2013.01); *A61K 38/063* (2013.01)

(58) Field of Classification Search
  CPC .... A61K 38/28; A61K 9/0043; A61K 38/063; A61P 25/16
  See application file for complete search history.

(56) References Cited

U.S. PATENT DOCUMENTS

| | | |
|---|---|---|
| 5,762,922 A | 6/1998 | Noble et al. |
| 7,875,273 B2 | 1/2011 | Messina et al. |
| 8,362,080 B2 | 1/2013 | Sekhar |
| 8,987,199 B2 | 3/2015 | Abdel Maksoud et al. |
| 9,084,760 B2 | 7/2015 | Sekhar |
| 2008/0078382 A1 | 4/2008 | LeMahieu et al. |
| 2011/0305751 A1 | 12/2011 | Gaillard |

FOREIGN PATENT DOCUMENTS

WO    0202190 A2    1/2002

OTHER PUBLICATIONS

Athauda et al., "Insulin resistance and Parkinson's disease: A new target for disease modification?" Progress in Neurobiology, 2016, 145-146: 98-120. (Year: 2016).*
Katakam et al., "Insulin-induced generation of reactive oxygen species and uncoupling of nitric oxide synthase underlie the cerebrovascular insulin resistance in obese rats," Journal of Cerebral Blood Flow & Metabolism, 2012, 32: 792-804. (Year: 2012).*
Clinical Trials NCT01177319, www.clinicaltrials.gov, pp. 1-6, Aug. 9, 2010 (Year: 2010).
Mischley et al., "Central Nervous System Uptake of Intranasal Glutathione in Parkinson's Disease," Nature Partner Journal-Parkinson's Disease, 2016, 2: 1-6 (Year 2016).
Mischley LK, "Phase IIB Study of Intranasal Glutathione in Parkinson's Disease," The Michael J. Fox Foundation, 2014, pp. 1-5, (Year: 2014).
Clinical Trials NCT04251585, www.clinicaltrials.gov, pp. 1-10, Feb. 5, 2020, (Year: 2020).
Goldstein, Barry J. et al., Redox Paradox: Insulin Action is Facilitated by Insulin-Stimulated Reactive Oxygen Species With Multiple Potential Signaling Targets, National Institute of Health, Diabetes. Feb. 2005; 54(2): 311-321.
Van Der Heide, L.P. et al., Insulin Inhibits Extracellular Regulated Kinase 1/2 Phosphorylation in a Phosphatidylinositol 3-Kinase (P13) Kinase-Dependent Manner in Neuro2a Cells, Journal of Neurochemistry, (2003) 86, 86-91.

* cited by examiner

*Primary Examiner* — Julie Ha
(74) *Attorney, Agent, or Firm* — Christopher & Weisberg, P.A.

(57) ABSTRACT

A method for treating Parkinson's disease where insulin and GSH may be administered intranasally. The GSH and insulin that is administered may be in varying doses at least once daily. The GSH and insulin may be administered sequentially and/or simultaneously and the medications may be administered for differing periods of time depending upon a patient's tolerance and response to the GSH and insulin. The GSH and the insulin may be administered for a certain period of time and/or indefinitely.

1 Claim, 3 Drawing Sheets

METHOD OF TREATING PARKINSON'S DISEASE WITH INTRANASAL DELIVERY OF INSULIN AND GLUTATHIONE

CROSS-REFERENCE TO RELATED APPLICATION

This application is a divisional of U.S. patent application Ser. No. 17/584,468, filed Jan. 26, 2022 and claims priority to U.S. Provisional Patent Application No. 63/153,422, filed Feb. 25, 2021, entitled "METHOD OF TREATING PARKINSON'S DISEASE WITH INTRANASAL DELIVERY OF INSULIN AND GLUTATHIONE," the entirety of which is incorporated herein by reference.

STATEMENT REGARDING FEDERALLY SPONSORED RESEARCH OR DEVELOPMENT n/a

TECHNICAL FIELD

This disclosure relates to a method of treating neurological disorders and diseases by intranasal delivery of therapeutics.

INTRODUCTION

Parkinson's disease is a neurological disorder that affects dopamine-producing neurons in a specific region of the brain, the substantia nigra. The disease is the second-most common neurodegenerative disorder, and the incidence of Parkinson's disease increases with age. The cause of the disease still remains largely unknown and can be challenging to diagnose and manage. The disease is chronic and progressive, and no cure presently exists.

Some of the telltale symptoms of Parkinson's disease include rigid muscles which can happen on almost any muscle in the body, slow movements where simple acts, like buttoning a shirt, take much longer than usual, tremors where certain portions of the body are shaky when they are not in use, walking and balance problems, as well as a host of other issues including depression, constipation, anxiety, fatigue, sleep problems, and bladder issues. These symptoms can affect every aspect of the life and can make day-to-day living very difficult.

Parkinson's disease cannot be cured currently, but some medications can help control the symptoms and make them more manageable. Presently, some of the available treatments can help with tremors, stuff muscles, and slow movements. Physical therapy, occupational therapy, speech therapy, surgery and other treatments are also available to try and manage the symptoms. Additionally, eating certain foods and exercise can help calm some of the symptoms of the disease.

The available medications to help treat and/or manage Parkinson's disease can have significant side-effects and patients have to work with their doctors to find a treatment plan that offers relief from symptoms with the fewest possible side effects. Determining the best treatment plan for a patient often involves trial and error and results in a cocktail of different medications and other treatments/therapies to help ease symptoms and improve the quality of life. Treatments for a patient may evolve and change over time given the progressive nature of Parkinson's disease.

Medications for Parkinson's disease can be cumbersome and difficult to take. Additionally, with the complex behavioral changes related to the disease, it can be difficult for a patient to routinely follow a given treatment plan to try and lessen the symptoms of the disease.

SUMMARY

The present disclosure advantageously provides a method for the treatment of Parkinson's disease, the method comprises: administering glutathione ("GSH") intranasally; and administering insulin and GSH intranasally.

In one aspect of the embodiment, the method may include GSH being administered intranasally at least once daily with a total dose of 400 milligrams ("mg") daily.

In one aspect of the embodiment, the method may include GSH being administered intranasally at least three times daily with a total dose of 400 mg daily.

In one aspect of the embodiment, the method may include GSH being administered intranasally with at least 280 mg per dose at least three times daily.

In one aspect of the embodiment, the method may include GSH being administered for at least ninety days.

In one aspect of the embodiment, the method may include insulin which is at least 40 International Units ("IU").

In one aspect of the embodiment, the method may include insulin administered intranasally at least once daily.

In one aspect of the embodiment, the method may include the administration of insulin and GSH intranasally for at least twelve weeks.

In another embodiment, a method for the treatment of Parkinson's disease comprises administering GSH intranasally; and administering insulin intranasally.

In one aspect of the embodiment, the GSH may be intranasally administered at least two times daily.

In one aspect of the embodiment, at least 280 mg of GSH may be administered intranasally at least two times daily.

In one aspect of the embodiment, the GSH and insulin may be administered for at least twelve weeks.

In one aspect of the embodiment, the insulin may be at least 40 IU.

In one aspect of the embodiment, the insulin may be administered intranasally at least two times daily.

In one aspect of the embodiment, 20 IU of insulin may be administered intranasally at least twice daily.

In one aspect of the embodiment, the administration of the insulin and the GSH intranasally is for at least twenty-four weeks.

In yet another embodiment, a method for treating Parkinson's disease may comprise administering GSH intranasally daily with at least two daily 280 mg doses for at least twenty-four weeks; and administering insulin 40 IU daily with at least two daily doses for at least twenty-four weeks.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

Figure 1:
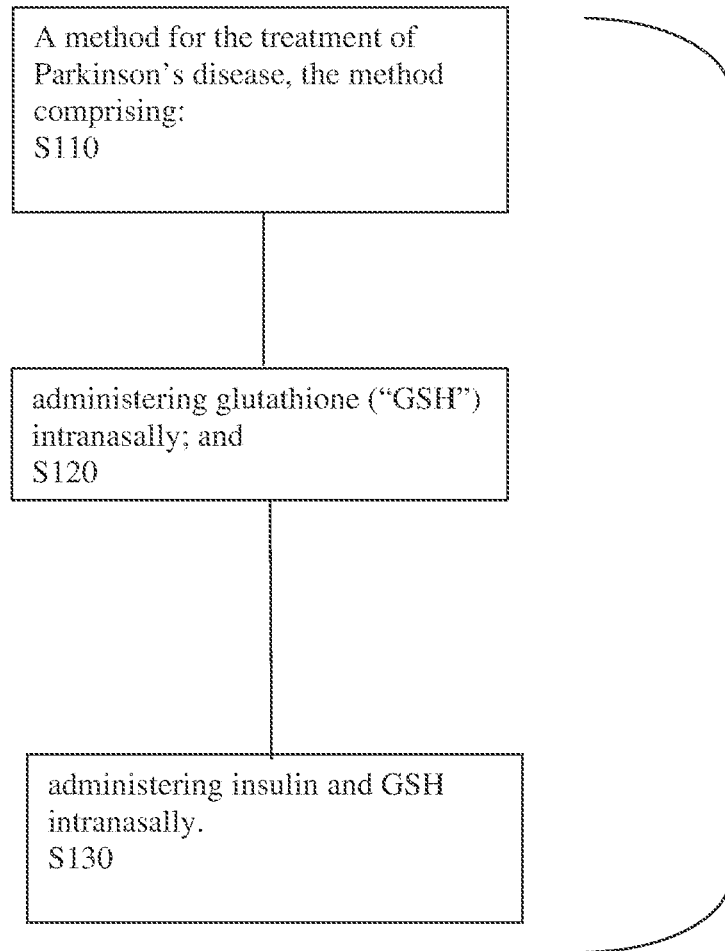
FIG. 1 shows an exemplary method for the treatment of Parkinson's disease.

Before describing in detail exemplary embodiments, it is noted that the embodiments reside primarily in combinations of methods related to treating neurological diseases, including Parkinson's disease, with intranasal delivery of insulin and glutathione ("GSH"). Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

The embodiments provide systems and methods for treating patients with neurological disorders, including Parkinson's disease ("PD"), with GSH and insulin. PD is a common chronic neurodegenerative disease that is often treated with different pharmaceutical agents intended to try and lessen some of the symptoms temporarily. Evidence has indicated that insulin may influence several processes in the brain including maintenance of synapses and pathways involving cogitation. GSH may serve as an important antioxidant, particularly in patients with PD, which is important for maintaining redox homeostasis, clearing metabolic waste, and serving as a reservoir for amino acids in the central nervous system ("CNS").

Referring now to the drawings in which like reference designators refer to like elements, there is shown in FIG. 1 an exemplary method in accordance with the principles of the present application. In FIG. 1, there are various steps shown in the exemplary method for the treatment of Parkinson's disease where S110 refers to step 1 of the method, S120 refers to step 2 of the method, and S130 refers to step 3 of the method. The method for the treatment of Parkinson's disease S110 may include administering GSH intranasally S120. GSH may be a tripeptide comprised of cysteine, glutamic acid, and glycine and is generally present in most mammalian tissue. GSH may function as an antioxidant, a free radical scavenger, and a detoxifying agent.

GSH may be administered in a variety of different manners including, but not limited to, intravenously by injection, orally, and intranasally. As a non-limiting example of how GSH may be administered, a ViaNase™ Electronic Atomizer may be used for an intranasal delivery of medication or GSH may be nebulized or aerosolized as well.

The intranasal administration of the medicine may include aerosol in a mist and/or larger droplets as administration using an aerosol may have favorable pharmacokinetics in terms of central nervous system penetration. For example, intranasal administration may allow the GSH to bypass the blood-brain barrier via the nasal cavity. The vascular makeup of the nasal cavity provides a route into the blood stream for medications that easily cross mucous membranes. Additionally, the direct absorption of medication into the blood stream may avoid gastrointestinal destruction and destruction of drugs by liver enzymes. Accordingly, the intranasal delivery of GSH as well as other drugs may make the drug more effective in the body. Furthermore, the rates of absorption of intranasal medications are typically better than subcutaneous or intramuscular routes. It may also be safer, easier, and more convenient for patients to take a medication intranasally, especially those that have an altered mental status.

Different doses of the GSH may be administered to a patient. As a non-limiting example, one dose may be administered to a patient or multiple doses may be administered. In an exemplary embodiment, the patient may receive two daily doses with 280 milligrams ("mg") of GSH per dose intranasally with a total of 400 mg of GSH daily or the patient may receive three daily doses of GSH intranasally with a total of 400 mg of GSH daily. Alternatively, the patient may receive three daily intranasal doses of 280 mg per dose with a total dose of 600 mg of GSH daily. More or less daily doses may be received by the patient and the total mg of GSH administered to the patient may also vary depending upon the patient's response to the GSH. The GSH may be administered using the same mg dosing daily or a varying mg dosing each day. For example, in a patient receiving two daily doses, one dose may be for 100 mg of GSH and a second dose of GSH may be for 300 mg of GSH. Additionally, a patient may receive different doses of GSH daily, for example, receiving 400 mg of GSH on one day and then receiving 600 mg of GSH on another day. Sensitivity and responsiveness to the GSH may drive when and how GSH dosing is provided to a patient.

The GSH may be administered to the patient over varying amounts of time. For example, the patient may receive GSH over a period of time to understand the safety, efficacy, and tolerability of the medication for the patient. The GSH may be administered for a certain period of time and/or indefinitely. In an exemplary embodiment, the GSH may be administered for a period of ninety days to evaluate a patient's response to the administration. Varying amounts of time may be used to administer the medication and could be significantly less or more time than ninety days. If a patient is not tolerating the GSH, the patient may either stop taking the GSH temporarily or alternatively may stop the medication permanently. Additionally, the amount of GSH given to the patient intranasally may vary depending on patient tolerance.

Also, insulin and GSH may be administered intranasally S130 to the patient. This may occur before, at the same time, or after the administration of the GSH intranasally. Insulin may play a role in regulating neuronal survival and growth, dopaminergic transmission, and in the maintenance of synapses. Different strengths and types of insulin may be used. As a non-limiting example, human insulin may be used which is created using DNA recombinant technology. In an exemplary embodiment, insulin at a strength of 40 International Units/milliliter ("IU/ml") or insulin at a strength of 20

IU/ml, 160 IU/ml, 100 IU/ml or 500 IU/ml may be used. The strength of the insulin used may depend on the patient's tolerance to insulin. Additionally, varying doses of insulin may be used depending upon the requirements of the particular patient. For example, a patient may be resistant to insulin, have diabetes, or another medical condition which may impact when, how, and how much insulin is administered.

The insulin may be delivered intranasally but may also be delivered via an injection using a syringe, injection pen, an insulin pump, or orally. The intranasal delivery of insulin may enhance long-term memory of a person and positively affect mood. Intranasal insulin administration may also result in direct insulin transport from the nasal cavity to the central nervous system via intraneuronal and extraneural pathways. In an exemplary embodiment, 20 IU of insulin may be delivered intranasally in two daily doses or 40 IU of insulin may be delivered in one daily dose. In alternative embodiments, the insulin may be delivered in different strengths and may be given in greater or fewer than two daily doses.

The administration of the GSH and insulin intranasally may be done over differing periods of times depending on the patient's response and tolerance to the medications. The GSH and insulin may be administered in a variety of different ways for a certain period of time and/or indefinitely. As a non-limiting example, the GSH and the insulin may be administered intranasally for a period of at least twelve weeks. The GSH and insulin may also be administered over differing periods of time. For example, the GSH may also be administered intranasally for twelve weeks and the insulin may be administered intranasally for fourteen weeks.

When the GSH and insulin are administered to the patient, the GSH may be given to a patient in varying amounts and one time daily or more than one time daily. The insulin and the GSH may be administered sequentially and/or simultaneously. For example, the GSH and insulin may be administered intranasally together, the GSH may be administered intranasally and then the insulin may be administered intranasally to the patient, or the insulin may be administered intranasally and then the GSH may be administered intranasally to the patient.

In an exemplary embodiment, the GSH may be administered intranasally in two daily doses. 280 mg of GSH may be administered to the patient in each dose totaling 400 mg of GSH in one day. The GSH may not be administered in the same dosing each time and different doses may be used throughout the day or may be changed depending upon the patient's response to the medication. As a non-limiting example, GSH may be administered intranasally at least once daily with a total dose of 400 mg daily, the GSH may be administered intranasally at least two times daily with a total dose of 400 mg daily, or the GSH may by administered intranasally with at least 280 mg per dose at least two times daily.

Figure 2:
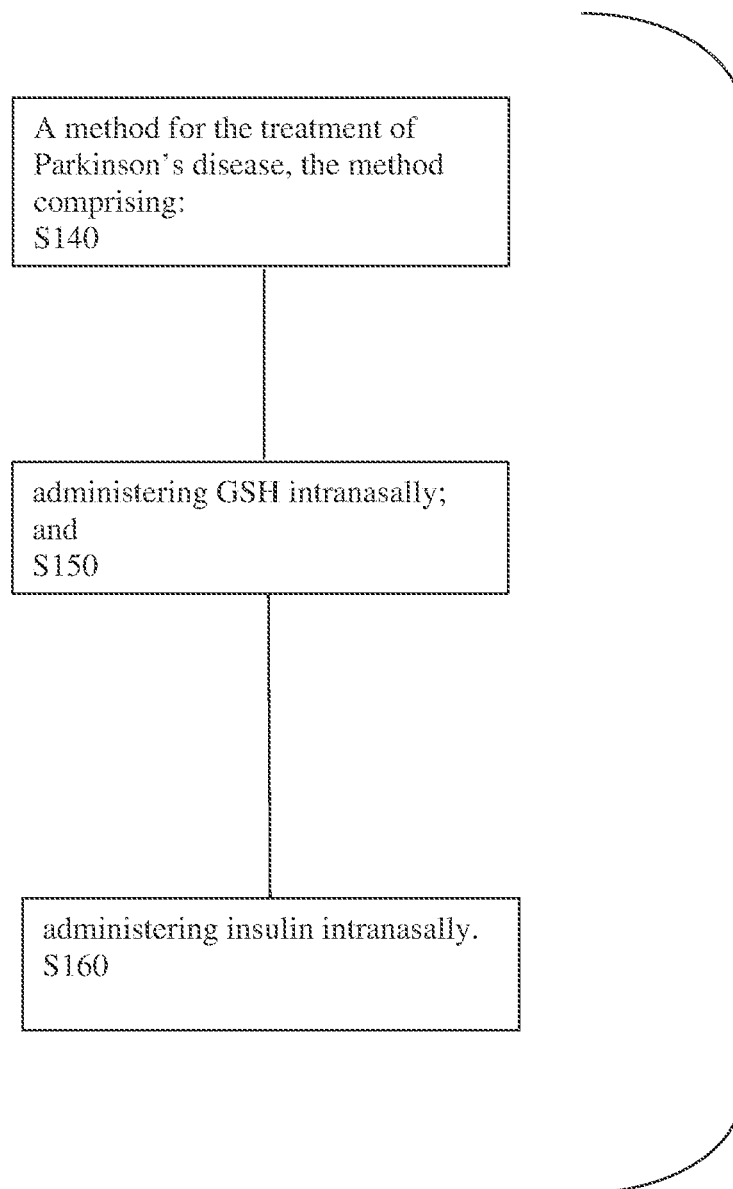
FIG. 2 shows an exemplary method for the treatment of Parkinson's disease.

Referring now to FIG. 2, in this embodiment, there are various steps shown in the exemplary method for the treatment of Parkinson's disease where S140 refers to step 1 of the method, S150 refers to step 2 of the method, and S160 refers to step 3 of the method. The method for the treatment of PD S140 may include administering GSH intranasally S150 and administering insulin intranasally S160. The GSH and insulin may be delivered intranasally simultaneously and/or sequentially, such that the GSH and insulin may be administered intranasally together, the GSH may be administered intranasally and then insulin may be administered intranasally to the patient, or the insulin may be administered intranasally and then the GSH may be administered intranasally to the patient.

As a non-limiting example, the GSH that is administered may be done at least two times daily wherein at least 280 mg is administered intranasally in each dose. The GSH may be administered for at least twelve weeks, but the time period may be longer or shorter as well.

The insulin may be 40 IU, but different strengths and types of insulin may be used depending upon a patient's tolerance to insulin and the patient's response to the insulin. For example, insulin may be administered intranasally at least twice daily, but this may be more or less frequent depending upon the particular patient and their sensitivity and/or responsiveness to the insulin. The administration of the insulin and the GSH may be for at least a period of twenty-four weeks, but it may also be a longer or shorter period of time depending upon the particular patient.

Figure 3:
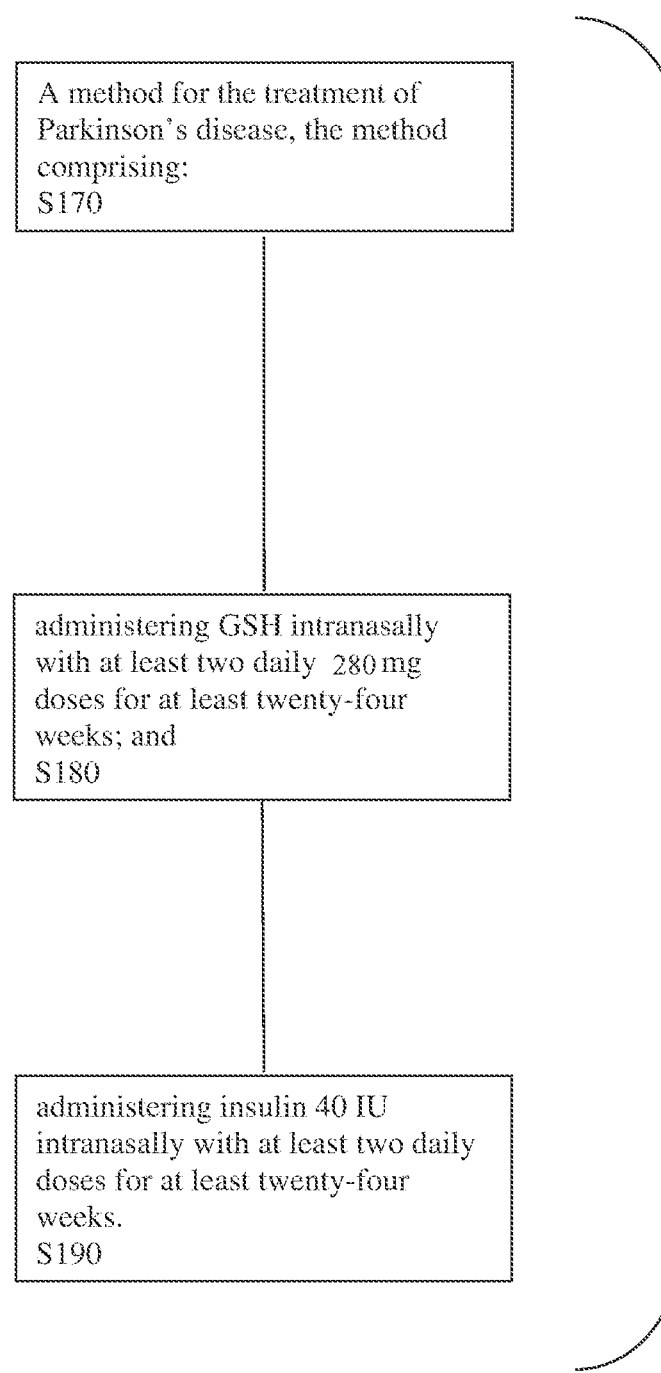
FIG. 3 shows an exemplary method for the treatment of Parkinson's disease.

Referring now to FIG. 3, in this embodiment, there are various steps shown in the exemplary method for the treatment of Parkinson's disease where S170 refers to step 1 of the method, S180 refers to step 2 of the method, and S190 refers to step 3 of the method. The method for the treatment of Parkinson's disease S170 may include administering GSH intranasally daily with at least two daily 280 mg doses for at least twenty-four weeks S180 and administering insulin 40 IU intranasally daily with at least two daily doses for at least twenty-four weeks S190. The GSH and the insulin may be administered together or at different times. Additionally, the dosing of the GSH and the insulin may be variable depending upon the particular patient.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

What is claimed:

1. A method for the treatment of Parkinson's disease, the method comprising:
    administering glutathione ("GSH") intranasally with at least two daily doses of 200 milligrams ("mg") for at least twenty-four weeks; and
    administering insulin 40 international units ("IU") daily for at least twenty-four weeks.

\* \* \* \* \*